United States Patent [19]

Grane et al.

[11] 4,296,262

[45] Oct. 20, 1981

[54] MANUFACTURE OF TERTIARY BUTYL ALCOHOL

[75] Inventors: Henry R. Grane, Springfield; John C. Jubin, Jr., Wallingford; G. Richard Worrell, Media, all of Pa.

[73] Assignee: Atlantic Richfield Company, Los Angeles, Calif.

[21] Appl. No.: 124,404

[22] Filed: Feb. 25, 1980

Related U.S. Application Data

[63] Continuation-in-part of Ser. No. 45,365, Jun. 4, 1979, abandoned.

[51] Int. Cl.³ .................................................... C07C 29/50
[52] U.S. Cl. ........................................... 568/910; 44/54
[58] Field of Search ........................................... 568/910

[56] References Cited

U.S. PATENT DOCUMENTS

| | | | |
|---|---|---|---|
| 2,653,962 | 9/1953 | Mitchell et al. | 568/910 |
| 2,845,461 | 7/1958 | Winkler et al. | 568/910 |
| 2,862,973 | 12/1958 | Winkler et al. | 568/910 |
| 3,360,585 | 12/1967 | Winnick | 568/910 |
| 3,391,214 | 7/1968 | Fetterly | 568/910 |
| 3,470,239 | 9/1969 | Russell | 568/910 |
| 3,478,108 | 11/1969 | Grane | 568/910 |
| 3,816,548 | 6/1974 | Williams et al. | 568/910 |
| 3,825,605 | 7/1974 | Johnston | 568/910 |
| 3,829,510 | 8/1974 | Adams et al. | 568/910 |
| 3,836,603 | 9/1974 | Conner et al. | 568/910 |

FOREIGN PATENT DOCUMENTS 1016035  1/1966  United Kingdom ................ 568/910

OTHER PUBLICATIONS

Winkler et al., "Ind. & Eng. Chem.", vol. 53 (1961), pp. 655-658.

Primary Examiner—Joseph E. Evans
Attorney, Agent, or Firm—John R. Ewbank

[57] ABSTRACT

Isobutane is injected into a liquid mixture concurrently with the injection of an oxygen-containing gas. Molybdenum catalyst is present. The oxidation is selective for the formation of tertiary butyl alcohol (TBA) so that the proportions of tertiary butyl hydroperoxide (TBHP), acetone, methanol, carbon dioxide or other less desirable products are relatively low. The tertiary butyl hydroperoxide produced by the reaction and/or the di-tertiary butyl peroxide in the reaction mixture remain in the reaction mixture while continuously distilling a product stream rich in tertiary butyl alcohol and those components boiling below TBA. After appropriate processing, such product stream is utilized as a blending component for gasoline.

1 Claim, 1 Drawing Figure

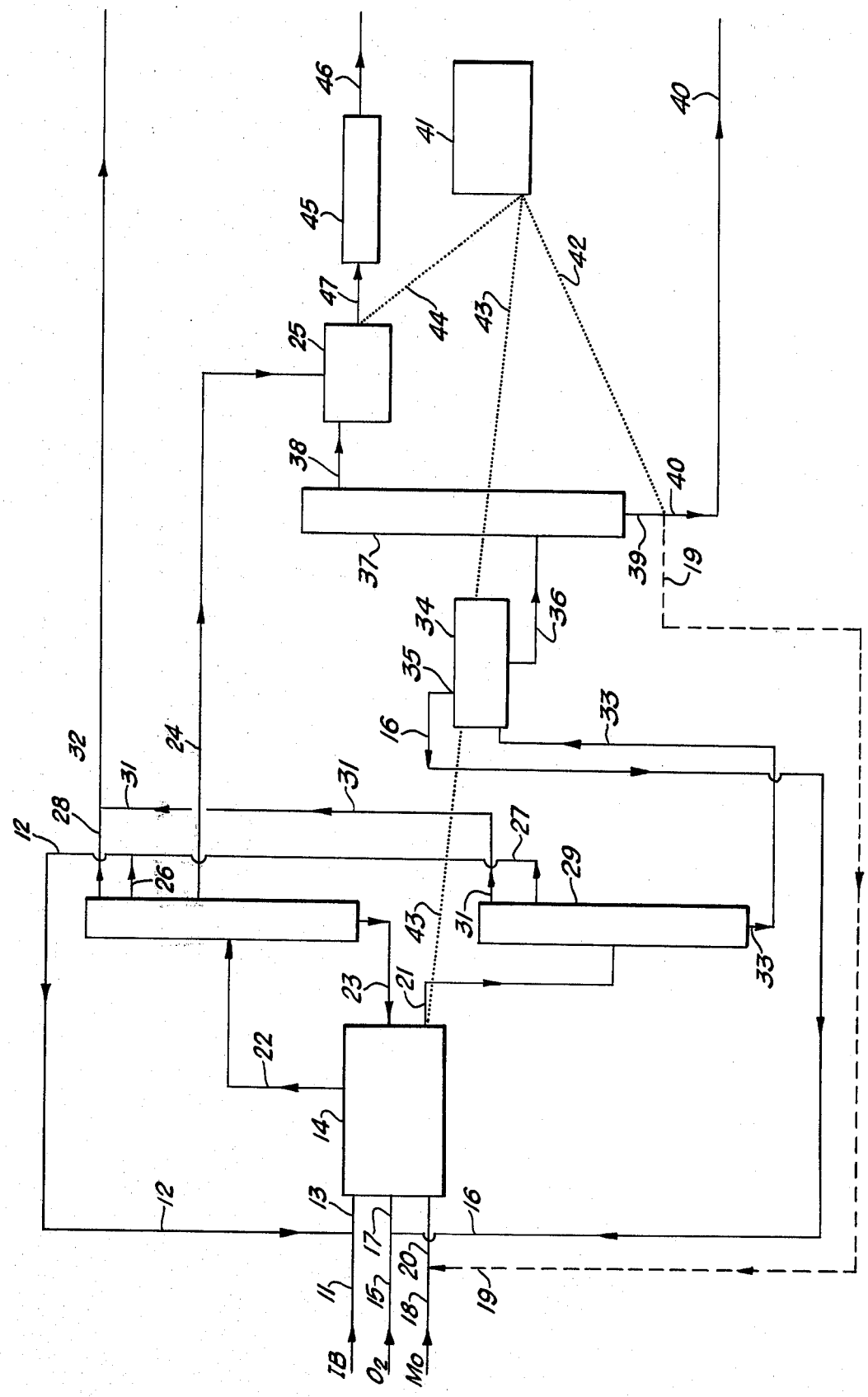

MANUFACTURE OF TERTIARY BUTYL ALCOHOL

RELATED APPLICATIONS

This is a continuation-in-part of Ser. No. 45,365 filed June 4, 1979, now abandoned.

Reference is made to the applications of Henry R. Grane, John C. Jubin, Jr. and G. Richard Worrell concerning similar subject matter, all the disclosure of which is deemed here reiterated and incorporated herein, said applications including "Preparing Oxygen Containing Fuel", Ser. No. 045,454 filed June 4, 1979, now abandoned and "Removing Water from Tertiary Butyl Alcohol", Ser. No. 051,561 filed June 25, 1979, now U.S. Pat. No. 4,239,926.

BACKGROUND OF INVENTION

1. Field of Invention

This invention relates to the preparation of mixtures containing a predominant amount of tertiary butyl alcohol by the oxidation of isobutane, and to the utilization of a mixture comprising tertiary butyl alcohol as a component in a blended gasoline.

2. Prior Art

Robertson et al U.S. Pat. No. 2,780,654 employs benzene as a solvent in oxidizing a mixture of isobutane and isobutene to a mixture of TBA and isobutylene glycol.

Winkler et al U.S. Pat. No. 2,845,461 oxidizes liquid isobutane in the absence of catalyst to prepare a mixture of TBA and TBHP.

Johnston U.S. Pat. No. 3,825,605 oxidizes isobutane to TBA using a solid catalyst comprising molybdenum oxide, and minor amounts of two other metals (from a group comprising cobalt, iron or chromium).

Kozlowski et al U.S. Pat. No. 3,832,149 prepares a motor fuel consisting of a mixture of alkylate and an oxylate prepared by hydrogenating the oxidate derived from oxidizing isobutane.

Barone U.S. Pat. No. 3,974,228 employs a buffer such as lanthanum carbonate in oxidizing isobutane to TBHP.

Brownstein et al U.S. Pat. No. 4,028,423 oxidizes isobutane to TBA and TBHP using a copper polyphthalocyanine catalyst activated with an aromatic amine.

There is a demand for a method of manufacturing tertiary butyl alcohol and/or products rich in tertiary butyl alcohol by the oxidation of isobutane.

SUMMARY OF THE INVENTION

In accordance with the present invention, a stream is distilled overhead from a reaction zone in which isobutane reacts with oxygen gas in a liquid comprising tertiary butyl alcohol (TBA) to produce TBA. Such overhead stream comprises oxygen, carbon dioxide, unreacted isobutane, TBA, and some byproducts. Such overhead stream is selectively condensed to permit recycling of an isobutane stream, withdrawal of a stream comprising carbon dioxide, and utilization of a liquid stream comprising TBA.

A slip stream of the liquid reaction mixture is withdrawn from the reaction zone and directed to a separation zone, from which isobutane is recycled to the reaction zone, from which a carbon dioxide-containing stream is withdrawn, and from which a liquid stream comprising TBA is directed to a decomposition zone. The tertiary butyl hydroperoxide (TBHP) content of the liquid is decomposed by hot aging at 200°–350° F. at a pressure lower than in the oxidation reaction zone. The liquid leaving the decomposition zone is distilled to provide an overhead stream comprising predominantly TBA.

The residual liquid from such distillation contains only a small fraction of the TBA derived from the decomposition zone. However, the weight of TBA in the residual liquid is greater than the weight of TBHP in such residual liquid.

The oxidation reaction zone is maintained at a temperature within a range from about 240° to about 340° F. at a pressure within a range from about 100 to 1000 psig. The residence time in the reactor is within a range from about 1 to 10 hours. The concentration of the soluble molybdenum catalyst is from about 1 to about 500 ppm of isobutane. The decomposition zone is maintained at a temperature within a range from about 200° F. to about 350° F. for a residence time of from about 1 to about 6 hours. The pressure in the decomposition zone is less than in the oxidation zone.

The TBA-containing streams derived from the overhead and from the liquid are combined in a merging zone at an appropriate stage. Among the final steps for the merged stream are a cleanup zone in which minor amounts of TBHP are decomposed and a blending zone in which the TBA is mixed into gasoline.

The nature of the invention is further clarified by reference to a plurality of examples.

DESCRIPTION OF EMBODIMENTS

EXAMPLE I

An oxidation reactor is maintained at 1000 psig at 335° F. The liquid in the reactor comprises isobutane, acetone, methanol, tertiary butyl alcohol, tertiary butyl hydroperoxide, water, and related byproducts. A mixture of fresh isobutane and recycle isobutane is injected into the reactor liquid. An oxygen containing gas is injected into the liquid reaction mixture, which contains 5 ppm of soluble molybdenum catalyst. The average residence time for the isobutane in the reactor is about 2 hours, and the extent of conversion of the isobutane is about 37%. The byproducts and products from such oxidation of isobutane include tertiary butyl alcohol (TBA), tertiary butyl hydroperoxide (TBHP), acetone, and a mixture of water, methanol, and related components. In addition to such liquid products, there are also carbon monoxide and carbon dioxide as by-products which are gaseous at ambient conditions. The liquid reaction mixture can be deemed to be about 63% isobutane and about 37% of said liquor mixture of products and byproducts. The reactor is maintained and operated in the manner corresponding generally to the operation of the reactors for production of a mixture of TBHP and TBA except that; (a) a molybdenum catalyst is present; (b) the temperature is higher; (c) a portion of the product is withdrawn from the reactor by distillation with only a supplemental portion withdrawn as a liquid, and (d) the rate of product withdrawal is greater so that the residence time is less than when the process is aimed particularly at TBHP. The liquid reaction mixture is adequately agitated so that the average composition of the reaction mixture and the composition of the slip stream from the reactor may be treated as identical.

The supplemental portion of the product withdrawn as a liquid stream from the oxidation zone is directed through a plurality of stages of debutanization so that from the reactor effluent the isobutane is separated and directed toward the pumps which recycle the isobutane to the reactor. The debutanized mixture from the oxidation zone is directed to a decomposition zone to form predominantly TBA and oxygen.

A significant portion of the product is withdrawn as an overhead vapor stream, whereby there is some degree of separation of TBA, b.p. 181° F. from TBHP, b.p. 270° F. The concentration of the tertiary butyl hydroperoxide in the liquid can be maintained at a higher level in the liquid reaction mixture than in the distillate without any recycling of streams rich in tertiary butyl hydroperoxide. The presence of such tertiary butyl hydroperoxide is believed to be helpful in promoting conversion of isobutane to isobutyl alcohol. Although such increased TBHP concentration is attainable by recycling a stream rich in TBHP, certain advantages accrue from minimizing the withdrawal of TBHP from the reactor.

The overhead stream from the reactor can be fully condensed, and then subjected to appropriate stages of separation in a separation zone to provide a plurality of streams comprising an isobutane recycle stream. The process is more generically defined by reference to selectively condensing appropriate fractions from the overhead vapor stream.

A stream comprising TBA but containing minor amounts of acetone and methanol is selectively condensed from the stream taken overhead from the oxidation zone. A stream of isobutane is selectively condensed from the vapors flowing after selective condensation of (and depletion of) the TBA, and such isobutane stream is recycled to the oxidation zone. Carbon dioxide, nitrogen, oxygen, and carbon monoxide, are withdrawn from the isobutane depleted stream. The TBA stream recovered by distillation from the oxidation zone contains enough TBHP to make appropriate the utilization of a cleanup zone. The two streams comprising TBA, that is, the stream derived from the overhead (i.e., distillation) from the oxidation zone and the stream derived from the liquid slip stream from the oxidation zone, are combined in a merging zone at an appropriate stage of the total process. Ordinarily such merging zone is just prior to the cleanup zone. It is important that both the TBA streams (derived from the liquid and from the vapor from the oxidation zone) be treated at 375°–475° F. for from 1 to 10 minutes prior to using the TBA as a blending component for gasoline. Hence, the merging zone must be at a stage prior to such cleanup zone. It might sometime be appropriate to merge the TBA containing streams prior to the stage of the decomposition zone, and the flexibility concerning the placement of the merging zone is embraced by the generic terminology of placing the merging zone at least before the cleanup zone.

Because high boiling products other than TBHP form during oxidation and are not completely codistilled with the volatilized TBA, and because such high boiling products must not be allowed to accumulate in excessive concentrations in the liquid in the oxidation zone, it is necessary to withdraw a slip stream of liquid from the oxidation zone. The percentage of technical grade of TBA (including methanol and acetone) derived from the distillation from the reactor should ordinarily be 55–85% of the total TBA, and that derived from the slip stream should ordinarily be 15–45% of the total. However, monitoring of the slip stream to assure an appropriate concentration of said high boiling other products (i.e., excluding TBHP and TBA, but including other high boiling components of the oxidate) is the necessary requirement in regulating the proportions of liquid withdrawal. The concentration of such other high boiling products must be within a range from about 1% to about 10% of the oxidate, with the proportion of slip stream withdrawal increasing significantly whenever increases in concentration in the 6% to 10% range are detected, and with the proportions normally being adjusted so that such others concentration is in the range from about 4% to 6% of the oxidate.

The TBA containing stream from the distillation of vapor from the oxidation zone is a significant portion of the total TBA production. The TBA containing stream derived from the slip stream from the liquid in the oxidation zone is a supplemental portion of the production of TBA.

As previously noted, the slip stream, after being debutanized, is aged in the decomposition zone. The liquid withdrawn from the decomposition zone is directed to a distillation zone. A stream comprising TBA is withdrawn overhead from such post decomposition distillation. The detailed composition of the bottoms is affected by various modifications of such distillation, but the residual liquid assuredly contains TBHP, a unit weight ratio of TBA to TBHP greater than one, and the molybdenum catalyst. Ordinarily there is no recycle of any portion of such residual liquid, which can be disposed of as a fuel for use in burners coping with its soluble molybdenum content.

If desired, the distillation of the effluent from the decomposition zone can be precise enough, not merely to separate streams of acetone, methanol, and TBA (for subsequent mixing into a technical grade of TBA) but also to separate a stream of distillable high boiling byproducts comprising formic acid, which stream can be withdrawn from the system. A stream comprising TBHP, but containing a unit weight ratio of TBA to TBHP greater than one, and containing ditertiary butyl peroxide, but not contaminated by significant amounts of said distillable high boiling byproducts, constitutes the bottoms stream from such distillation. If desired, a portion of such bottoms can be recycled to the oxidation zone. Although there are various possible modifications of the distillation of the effluent from the decomposition zone, it is not permissible to provide for 100% recycle of the bottoms therefrom, and it is necessary to withdraw at least a portion (generally a major portion) of the residual liquid from such distillation.

A stream containing TBA is subjected to a cleanup treatment to decompose trace amounts of TBHP by heating under pressure at 375°–475° F. for from 1 to 10 minutes. The effluent from such cleanup zone is a fuel grade of TBA containing about 10% acetone and about 4% methanol.

The TBA containing stream derived from the overhead from the oxidation zone is mixed with the TBA containing stream derived from the slip stream in a merging zone. It is ordinarily desirable to have such merging zone at a stage just prior to the cleanup zone. However, the merging zone can be at any appropriate earlier stage, such as just prior to the decomposition zone, without jeopardizing the operativeness of the process.

EXAMPLE II

A large pressurized kettle has a stirrer maintaining a reasonably uniform mixture while reactants are injected into such liquid reaction mixture in laboratory preparation of tertiary butyl alcohol. A liquid stream (slip stream) of the reaction mixture is directed from the oxidation zone of said kettle to a debutanizing zone and then to a decomposition zone. A product stream comprising TBA is also withdrawn by distillation from the kettle. An automatic liquid level control maintains the amount of liquid in the autoclave at a predetermined height. The rate of removal of vapor and the rate of transfer of liquid stream are regulated in response to the combination of factors comprising reaction rate, temperature, pressure, and reactant injection rate. Air is injected into the liquid to oxidize components, thereby forming a nitrogen-containing effluent gas. A series of partial condensers desirably are positioned between the vapor zone of the autoclave and the gas pressure regulator. The gas withdrawn from the regulator consists of the fixed gases such as carbon dioxide, carbon monoxide, air, oxygen, etc. The gaseous effluent from the autoclave (via such series of condensers) can go through a pressure regulator maintaining the autoclave at a predetermined elevated pressure.

Isobutane is injected into a stirred, pressurized kettle at 295° F. at 1000 psig of a distillation system adapted to distill TBA from a liquid reaction mixture containing TBHP and more TBA then TBHP and more isobutane than the combination of TBA and TBHP. The injected isobutane is a mixture of fresh isobutane and recycle isobutane. Air is injected into the liquid contents of the reactor with unreacted oxygen and nitrogen withdrawn along with carbon dioxide from the pressure regulating system. The residence time is about 3.5 hours. About 75% of the liquid oxidate is TBA. The reaction mixture comprises about 30% oxidate and about 70% isobutane.

The slip stream of liquid is transferred from the oxidation zone and directed through three stages of pilot plant debutanization, with the isobutane being pumped back to the oxidation zone. The debutanized effluent at about 100 psig is directed to the decomposition zone, an autoclave functioning in a manner generally similar to the autoclave employed as the oxidation reactor. The debutanized oxidate is maintained in the decomposition reactor for about 3.5 hours residence time. The liquid effluent stream from the decomposition zone consists of a mixture of about 80% TBA, about 0.5% TBHP, about 10% acetone, about 5.5% methanol, about 2% water, and about 2% other high boiling byproducts. Such liquid effluent is distilled to provide a TBA containing stream. Acetone and methanol impurities may be separated and subsequently injected into the TBA, or codistilled therewith. The residual liquid, containing a greater weight of TBA than TBHP, containing other high boiling byproducts, and molybdenum catalyst, is directed for use as a component of fuel oil in an industrial burner in which the presence of the molybdenum is tolerable.

The product stream comprising TBA distills overhead from the oxidation zone, which is maintained at 295° F. and 1000 psig partly for the purpose of refluxing back into the liquid reaction mixture a significant portion of any TBHP which might be volatilized. A stream comprising TBA, and usually also containing methanol and acetone is selectively condensed from the overhead from the distillation in the oxidation zone. A liquid isobutane is selectively condensed from the overhead vapor stream from the oxidation zone. Such TBA containing stream is directed to a merging zone, which is desirably staged just prior to the cleanup zone. Alternatively, the merging zone can be staged just prior to the decomposition zone, or at any other stage prior to the cleanup zone.

After normally liquid components have been selectively condensed to prepare the TBA containing stream, and after the recycle isobutane stream has been selectively condensed, the overhead stream from the distillation of the oxidation zone consists of noncondensable gases comprising nitrogen, oxygen, carbon monoxide and carbon dioxide, which stream is withdrawn through a gas pressure regulating vent.

After the TBA containing stream derived from the liquid slip stream, and the TBA containing stream derived from the distillation in the oxidation zone have been merged, the combined streams are subjected to a cleanup treatment by heating at 375°–475° F. for from 1 to 10 minutes at superatmospheric pressure. After such heat treatment, the TBA stream is blended with naphtha and reformate to prepare gasoline, and enhances the octane thereof.

EXAMPLE III

An oxidation reaction zone is maintained at about 280° F. at a pressure of about 700 psig. The liquid reaction mixture consists of about 55.6% isobutane and 44.4% oxidate. The acetone concentration is 3.3%. The concentration of TBA is 25.0%. The TBHP concentration is 12.6%, providing a TBA/TBHP unit weight ratio of 2. The concentration of water, methanol, and other byproducts amounts to about 3.5%. The liquid contains 5 ppm of soluble molybdenum catalyst based upon the amount of liquid in the reaction zone. The residence time is about 4 hours.

A portion of the reaction mixture is vaporized from the reactor and directed through a total condenser to a distillation zone. The fractions separated by such distillation zone comprise a recycle isobutane stream and a stream consisting of a mixture of about 84.5% parts of TBA, 8% acetone, 2.8% methanol, 2.9% water, and 1.8% other byproducts. The liquid stream comprising TBA derived from the overhead from the oxidation zone is directed to a merging zone, in wich it is combined with a TBA containing stream derived from the liquid effluent from the oxidation zone.

The slip stream withdrawn from the oxidation zone is monitored both as to composition and as to flow rate, aiming to maintain a proportion of TBA directed to the merging zone from the liquid from about 15% to about 45% of the total rate of production of TBA. The flow rate of such liquid effluent from the oxidation zone is regulated to maintain a concentration of high boiling byproducts other than TBHP and TBA which is within a range from about 1% to about 10% of the oxidate. Such liquid effluent from the oxidation zone is directed through a debutanizer to a decomposition zone in which the TBHP is decomposed during a period of about 10 hours by heating at 280° F. at about 100 psig. The liquid oxidate (effluent from the oxidation zone after removal of all isobutane) consists of about 58% TBA, about 23.5% TBHP, about 4.3% each of acetone, methanol, and water, and about 5.6% others, and such liquid oxidate is about 23.4% of the product withdrawal or about one-third of the 76.6% of product withdrawal by vapor distilled from the oxidation zone. Data relating to recovery are:

| Component | Withdrawal as Liquid | Withdrawal as Vapor | Decomp. Zone | Product Total |
|---|---|---|---|---|
| TBHP | 5.5 | | | none |
| TBA | 13.6 | 63.7 | 4.1 | 81.4 |
| Acetone | 1.0 | 7.0 | .7 | 8.7 |
| Methanol | 1.0 | 2.2 | .3 | 3.5 |
| Water | 1.0 | 2.3 | .2 | 3.5 |
| Others | 1.3 | 1.4 | .2 | 2.9 |

After the merging of the TBA derived from the vapor and the TBA derived (via decomposition zone) from the liquid, the merged TBA stream is heated at 400° F. for 8 minutes to decompose any residual TBHP and to prepare a TBA suitable for use in the blending of gasoline.

EXAMPLE IV

The oxidation reaction zone is maintained at about 276° F. at about 800 psig. The liquid reaction mixture contains 5 ppm of solubilized molybdenum catalyst. The liquid contains about 13.7% TBHP.

The composition of the liquid in the reaction zone is about:

| Isobutane | 44.1% by weight |
|---|---|
| Acetone | 2.2 |
| TBA | 35.4 |
| TBHP | 13.7 |
| Others | 4.6 |

About half the product is withdrawn as vapor, and sent through a condenser, debutanizer, and distillation zone. The bottoms fraction from the distillation zone, comprising about 5 parts of TBHP and 7 parts of TBA is recycled to the oxidation reaction zone. The distillate stream comprises:

| | Parts |
|---|---|
| TBA | 31.9 |
| Acetone | 6.3 |
| Methanol | 2.0 |
| Water | 3.2 |
| Others | 0.8 |
| | 44.2 |

From the reaction zone there is also withdrawn 94.7 parts of said reaction mixture which is sent through a debutanizer removing 41.9 parts of isobutane for recycle. In the decomposition zone, 62.6 parts of liquid are heated for 4 hours at 270° F. to decompose about 92% of the 13 parts of TBHP, leaving a residue of about 1 part of TBHP. The thus prepared stream of TBA is mixed with the distillate derived from the vapor in a merging zone. The merged TBA streams are heated at from 375° to 475° F. for from 1 to 10 minutes under pressure to clean up the product by decomposing residual TBHP and/or related peroxy type compounds. Data relating to products are:

| | Withdrawal as Liquid | Withdrawal as Vapor | Decomp. Zone | Product Total |
|---|---|---|---|---|
| TBHP | 13.2 | | | None |
| TBA | 34.1 | 31.9 | 9.2 | 75.2 |
| Acetone | 2.1 | 6.3 | 3.5 | 11.9 |
| Methanol | NA | 2.0 | 2.0 | 4.0 |
| Water | NA | 3.2 | 1.0 | 4.2 |
| Others | 4.4 | 0.8 | 2.0 | 7.2 |

The partial withdrawal of the TBA as vapor and the recycling of some TBHP to the reactor promotes removal of TBA from the reaction zone promptly after initial formation. Because some TBHP decomposition occurs in the oxidation reaction zone, the zone for the subsequent decomposition of the TBHP content of withdrawn liquid can be smaller.

EXAMPLE 5

About 198 parts of isobutane plus 510 parts of air are supplied per hour to a pressurized reaction zone maintained at 285° F. and 500 psig. About 414 parts of fixed gases ($N_2$, $CO_2$, CO, etc.) are withdrawn through the regulator automatically maintaining the system at 500 psig. A vapor stream is distilled directly from the reaction mixture and subjected to a debutanization zone, thus providing a debutanized stream comprising 71.7 parts of TBA, 11 parts of TBHP, and 15.6 parts of others which debutanized stream is directed to a distillation zone. A distillate fraction comprising about 67.7 parts of TBA is recovered and directed to the merging zone. The bottoms fraction from such distillation zone, comprising 12 parts of TBA and 11 parts of TBHP is recycled to the oxidation reaction zone.

About 21.5 parts (a lesser stream) of liquid reaction mixture is withdrawn from the oxidation zone. This liquid, comprising 10.7 parts of TBA, 5.4 parts of TBHP, and 5.4 parts of others is transferred to a decomposition zone and aged to provide a stream of TBA directed to the merging zone, where it is mixed with the TBA stream derived from the vapor. The merged streams are heated at 375°–475° F. for 1 to 10 minutes to decompose residual TBHP. The thus prepared mixture of TBA, acetone, methanol, and the like is employed as a blending component to increase the octane number of gasoline.

Data relating to the thus prepared blending component include:

| | Withdrawals as Liquid | Withdrawals as Vapor | Decomp. Zone | Product Total |
|---|---|---|---|---|
| TBHP | 5.4 | | | None |
| TBA | 10.7 | 71.4 | 3.5 | 85.6 |
| Others | 5.4 | 15.6 | 1.9 | 22.9 |

The distillation of a portion of the TBA from the reactor permits the decomposition reaction zone to be smaller than it otherwise would be.

In the drawing, a stream of fresh isobutane 11 combines with a recycle IB stream 12 to provide a merged IB stream 13 directed into an oxidation zone 14. Fresh oxygen stream 15 combines with recycle $O_2$ stream 17 directed into the oxidation zone 14. Molybdenum catalyst stream 18 may, if desired, be merged with an optional catalyst recycle stream 19 (usually zero) before catalyst stream 20 enters reactor. Obviously various modifications of mixing and/or injection approaches are feasible, and the drawing is highly schematic to permit a general perspective on the overall process. For example, nitrogen can be included in the $O_2$ stream, as indicated by its presence in the exit gas stream.

In oxidation reaction zone 14, IB is oxidized to produce tertiary butyl peroxide (TBP, a component of HB, high boilers) tertiary butyl hydroperoxide (TBHP), formic acid (HCOOH), miscellaneous acids in the HB fraction, water ($H_2O$), tertiary butyl alcohol (TBA), methanol (MeOH), acetone ($Me_2CO$), carbon dioxide ($CO_2$) and carbon monoxide (CO). The reaction mixture comprises all said reactants and all said products, and is sufficiently well agitated that the composition of a slip stream 21 from oxidation zone 14 can be deemed to have the same composition as the lower liquid layer in oxidation zone. Above the liquid and froth is a vapor zone. An overhead stream 22 permits withdrawal from oxidation zone of a mixture of nitrogen, oxygen, carbon monoxide, carbon dioxide, isobutane, acetone, methanol, and TBA. Because acetone, methanol and TBA each form azeotropes with water, a portion of the water is thus distilled from oxidation zone 14 into overhead stream 22, but significant portions of the total water product are withdrawn through the slip stream 21.

The distillation of stream 22 from oxidation zone 14 is controlled for selectively retaining most of the TBHP in the oxidation zone 14 and favoring withdrawal of a portion of the TBA in the overhead stream 22. A reflux stream 23 returns to oxidation zone 14 a significant portion of any TBHP or other components boiling above TBA. It is convenient to conduct a series of successive selective condensation steps in a fractional distillation tower, but a series of dephlegmators could promote an equivalent series of selective condensation steps. Thus, the formation of the reflux stream 23 is a selective condensation step.

A condensed debutanized distillate TBA stream 24 is selectively condensed from the vapor subsequent to said separation of reflux stream 23. Such condensed debutanized distillate TBA stream 24 comprises acetone, methanol, water and TBA. Said stream 24 is directed to merging zone 25.

Isobutane is selectively condensed from the TBA-depleted overhead vapor stream to provide overhead IB stream 26. An isobutane stream 27 derived from slip stream 21 is merged with overhead IB stream 26 to provide the IB recycle stream 12.

A gaseous withdrawal stream 28 comprises nitrogen (present in at least measurable amounts in the air, commercial oxygen, mixture, or other $O_2$ feed stream 15), carbon monoxide, and carbon dioxide. As has been true of the gaseous withdrawal stream from liquid isobutane oxidation zones for many years, the equilibrium concentration of oxygen present in the vapor space of oxidation zone 14 corresponds approximately to the $O_2$ present in the gaseous withdrawal stream 28, inasmuch as the oxygen consumption rate is relatively slow (compared to consumption rate in oxidation zone 14) throughout the various steps of selective condensation at successively lower temperatures.

Attention is now directed to the oxidation zone 14 from which flows liquid as a slip stream 21 to debutanizing zone 29. Said debutanizing zone is adapted to permit the selective condensation of a debutanized TBA stream 33 and the selective condensation of said previously identified IB stream 27, which helps to form recycle IB stream 12. The liquid slip stream 21 contains some dissolved nitrogen, oxygen, carbon monoxide and carbon dioxide, and a stream of such gas is vented through line 31 to gas withdrawal line 28, where they merge to form gas withdrawal line 32. After liquid slip stream 21 has been debutanized in debutanizing zone 29, it flows as stream 33 to a decomposition zone 34. By treating the debutanized liquid at 200°–350° F. at 40–100 psig for 1–6 hours, some of the TBHP is decomposed to provide TBA and $O_2$. The thus generated $O_2$ can be recycled through controlled outlet 35 to $O_2$ recycle line 16.

After most of the TBHP has thus been decomposed, the liquid effluent stream 36 is directed from the decomposition zone 34 to distillation zone 37. An overhead stream 38 consists of acetone, methanol, and TBA. A bottoms stream 39 consists of a mixture of those components boiling above TBA plus a sufficient amount of TBA to assure a molar ratio of TBA to TBHP greater than one. The bottoms stream 39 can be sent through a divider to allocate a portion to catalyst recycle stream 19 and a portion to fuel withdrawal line 40.

Attention is called to a control system 41 adapted to maintain the concentration of HB (high boilers, comprising formic acid, other high boiling acids, etc.) within the liquid in oxidation zone within a range from 1% to 10% of the oxidate. At initial startup, it is appropriate to include about 32% TBA, about 2% water (a component of HB) and 66% IB as feedstock. Oxidation zone 14 is maintained at reasonably stable conditions, so that analyses of daily samples or hourly samples are usually adequate for fine tuning of the system. The drawing shows such control system generically to embrace either periodic sampling or continuous monitoring with feedback regulation of flow rates to maintain the HB concentration in the oxidate within the 1 to 10% range. Control system 41 functions because there are communication lines 42, 43, 44 to lines 39, 21, and 47 respectively. Control system 41 preferably maintains the concentration of HB in the oxidate at 4% to 6%. When there are favorable conditions throughout the system, keeping the HB concentration near 4%, then a fraction of such HB stream 39 can be diverted from fuel withdrawal line 40 and directed by catalyst recycle line 19 to oxidation zone 14.

The debutanized overhead distillate stream 24 is directed ordinarily to merging zone 25 for merging with stream 38 to provide merged stream 47 which is directed to cleanup zone 45. It would be less advantageous, but plausibly operable, to relocate the merging zone to feed into either line 33 or line 36, or to proportion stream 24 amongst 38, 33, 36, as embraced by the terminology relating to merging line 24 with a TBA containing stream derived from 21 at some stage prior to cleanup zone 45. That is, the debutanized distillate from the reactor stream is merged into stream providing TBA (e.g., 33, 36 and/or 38) to provide a stream containing TBA at some step prior to the directing of a TBA containing stream (i.e., 47) to a cleanup zone.

It should be noted that a cleanup zone 45 subjects the TBA to 375°–475° F. for 1–10 minutes, thereby decomposing TBHP residues. The liquid effluent stream 46 represents the principal product of the present invention, and is a TBA stream suitable for use in motor fuels. Such stream also contains $Me_2CO$ and MeOH.

The description of the drawing exemplifies some preferred embodiments of the invention, but is not intended to be limiting of the invention, which is defined in the appended claims. Various modifications of the invention are possible without departing from the scope of the appended claims.

The embodiments of the invention in which an exclusive property or privilege is claimed are defined as follows:

1. The method of preparing tertiary butyl alcohol (TBA) which includes the steps of:

maintaining in an oxidation reaction zone a liquid reaction mixture comprising TBA, tertiary butyl hydroperoxide (TBHP), and (TBHP) isobutane at conditions favoring the oxidation of isobutane to a mixture of TBA and TBHP, said conditions comprising a temperature within the range from about 240° F. to about 340° F., a pressure maintaining most of the isobutane in said oxidation reaction zone in the liquid phase, said pressure being within the range from about 100 psig to about 1000 psig, a residence time within the range from about 1 to about 10 hours, and a concentration of soluble molybdenum catalyst corresponding to about 1 to about 500 ppm of the weight of isobutane in said liquid;

refluxing back into said reaction mixture a significant portion of any TBHP or other components boiling above TBA, while withdrawing from the oxidation reaction zone an overhead vapor stream comprising nitrogen, carbon monoxide, carbon dioxide, isobutane, acetone, methanol, water, and TBA;

selectively condensing from said overhead vapor stream a condensed TBA stream comprising acetone, methanol, water and TBA;

selectively condensing isobutane from the TBA depleted overhead vapor stream and recycling such condensed isobutane to the oxidation reaction zone;

withdrawing an isobutane-depleted overhead vapor stream comprising nitrogen, carbon monoxide, carbon dioxide from said overhead vapor stream;

directing at a controlled rate a slip stream of liquid rection mixture from the oxidation reaction zone to a debutanizing zone in which the isobutane is selectively separated and recycled to the oxidation reaction zone, said slip stream being controlled to be sufficient to maintain in the liquid oxidate in the reaction zone a concentration of high-boiling byproducts from about 1% to about 10%, said high-boiling byproducts being those, other than TBHP and TBA, which are not completely codistilled with the TBA;

directing the debutanized slip stream to a decomposition zone maintained at a temperature from about 200° to 350° F. at a pressure from about 40 to about 100 psig for a residence time of from about 1 to about 6 hours to decompose a portion of the TBHP and to increase the TBA concentration;

directing the liquid effluent stream from the decomposition zone to a distillation zone to provide a distillate stream comprising acetone, methanol, and TBA, and to provide a residual liquid having a unit weight ratio of tertiary butyl alcohol to tertiary butyl hydroperoxide greater than one, byproducts which are not completely codistilled with tertiary butyl alcohol, and molybdenum catalyst;

withdrawing at least a portion of said residual liquid stream;

directing a stream containing TBA to a cleanup zone maintained at 375°–475° F. for from 1 to 10 minutes under pressure to decompose any TBHP residues;

directing to a gasoline-blending zone a stream comprising TBA derived from the effluent stream from said cleanup zone; and merging a debutanized distillate from the reactor overhead stream with a debutanized distillate derived from the slip stream to provide a stream containing TBA at some stage prior to the directing of a TBA containing stream to said cleanup zone.

* * * * *